United States Patent [19]

Foley et al.

[11] Patent Number: 4,962,197

[45] Date of Patent: Oct. 9, 1990

[54] PHOTO-INACTIVATION OF CANCER CELLS

[75] Inventors: James W. Foley; Louis Cincotta, both of Andover, Mass.

[73] Assignee: Rowland Institute for Science, Cambridge, Mass.

[21] Appl. No.: 157,214

[22] Filed: Feb. 12, 1988

[51] Int. Cl.⁵ .................. C07D 265/38; C07D 279/18
[52] U.S. Cl. .......................................... 544/31; 544/1; 544/99
[58] Field of Search ............................... 544/1, 31, 99

[56] References Cited

U.S. PATENT DOCUMENTS

| | | | |
|---|---|---|---|
| 2,528,863 | 11/1950 | Crossley et al. | 544/99 |
| 2,647,895 | 8/1953 | Crossley et al. | 544/99 |
| 4,651,739 | 3/1987 | Oseroff et al. | 128/395 |

FOREIGN PATENT DOCUMENTS 2083488 3/1982 United Kingdom .

OTHER PUBLICATIONS

Kikuchi et al., J. Photochemistry 16: 19–29 (1981).
Chibisov et al., J. C. S. Chem. Comm., pp. 1292–1293 (1972).
Drexhag, "Structure and Properties of Laser Dyes," in *Topics in Applied Physics*, pp. 14–15 (1977).
Lewis et al., Cancer Research 9: 736–740 (1949).
Bates et al., J. Neuropathology and Experimental Neurology 8: 411–418 (1949).
Fanghanel et al., J. Phys. Chem. 91: 3700–3703 (1987).
Lewis et al., Anatomical Records 95: 89–96, 96: 201–220 (1946).
Lewis et al., Anatomical Record 99: 369–377 (1947).

*Primary Examiner*—Richard L. Raymon
*Attorney, Agent, or Firm*—Fish & Richardson

[57] ABSTRACT

A compound having the formula

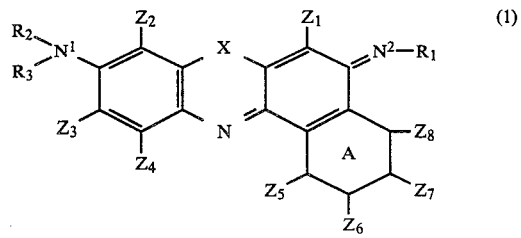

in which X is O, S, or Se; each $R_1$, $R_2$, and $R_3$, independently, is H, a lower alkyl, or aralkyl; A is a saturated or unsaturated ring; and each $Z_1$, $Z_2$, $Z_3$, $Z_4$, $Z_5$, $Z_6$, $Z_7$, or $Z_8$, independently, is H or a halogen, provided that when X is O, at least one group Z is a halogen; when either $Z_2$ or $Z_3$ is a halogen, at least one of $R_2$ or $R_3$ is H; and when both $Z_2$ and $Z_3$ are halogens, both $R_2$ and $R_3$ are H;

or a pharmaceutically acceptable salt thereof.

The compounds are useful for photo-inactivation of cancer cells.

13 Claims, 2 Drawing Sheets

FIG.1 □ LIGHT ▨ DARK

FIG.2 □ LIGHT-NO DYE ▨ DARK-DYE ▨ LIGHT-DYE

PHOTO-INACTIVATION OF CANCER CELLS

BACKGROUND OF THE INVENTION

This invention relates to photo-induced killing of cancer cells.

Photodynamic cancer therapy involves photosensitizing cancer cells with a compound and then killing the cells by exposing them to light, e.g., laser light. Oseroff et al., U.S. Pat. No. 4,651,739, for example, describes killing cancer cells by treating the cells with a cationic, lipophilic dye that is taken up and preferentially retained in the mitochondria of the cancer cells, and then exposing the cells to light.

SUMMARY OF THE INVENTION

In general, the invention features a compound having the formula (1)

in which X is O, S, or Se; each $R_1$, $R_2$, and $R_3$, independently, is H, a lower ($C_1$–$C_4$) alkyl, or aralkyl (having one aromatic ring, e.g., benzyl); A is a saturated ring (i.e. each carbon atom to which groups $Z_5$–$Z_8$ is attached are bonded to another such carbon atom in the ring through single bonds) or unsaturated ring (i.e. the ring contains 1 or 2 double bonds in addition to the double bond between ring A and the ring containing group $Z_1$); and each $Z_1$, $Z_2$, $Z_3$, $Z_4$, $Z_5$, $Z_6$, $Z_7$, or $Z_8$, independently, is H or a halogen (Cl, Br, or I), provided that when X is O, at least one group Z is a halogen; when either $Z_2$ or $Z_3$ is a halogen, at least one of $R_2$ or $R_3$ is H; and when both $Z_2$ and $Z_3$ are halogens, both $R_2$ and $R_3$ are H;

or a pharmaceutically acceptable salt thereof.

In preferred embodiments, the pka of $N^2$ preferably is between 5 and 11, inclusive, in aqueous solution.

In one preferred embodiment, X is O; $R_1$ is H; $R_2$ and $R_3$ are ethyl; $Z_1$ is I; ring A is an unsaturated ring having two additional double bonds; and $Z_2$–$Z_8$ are H. This compound has the formula (2)

and will hereinafter be referred to as "compound 2".

In another preferred embodiment, X is O; $R_1$ is H; $R_2$ is H; $R_3$ is ethyl; $Z_1$ and $Z_2$ are I; ring A is an unsaturated ring having two additional double bonds; and $Z_3$–$Z_8$ are H. The compound has the formula (3)

and will hereinafter be referred to as "compound 3".

In another preferred embodiment, X is O; $R_1$ is H; $R_2$ $R_3$ are ethyl; ring A is an unsaturated ring having two additional double bonds; $Z_6$ is I; and $Z_1$–$Z_5$ and $Z_7$–$Z_8$ are H. The compound has the formula (4)

and will hereinafter be referred to as "compound 4".

In another embodiment, X is O; $R_1$ is H; $R_2$ and $R_3$ are ethyl; $Z_1$ is Br; ring A is an unsaturated ring having two additional double bonds: and $Z_2$–$Z_8$ are H. The compound has the formula (5)

and will hereinafter be referred to as "compound 5".

In another preferred embodiment, X is O; $R_1$ is H; $R_2$ and $R_3$ are ethyl; $Z_1$ and $Z_6$ are I; ring A is an unsaturated ring having two additional double bonds; and $Z_2$–$Z_5$ and $Z_7$–$Z_8$ are H. The compound has the formula (6)

and will hereinafter be referred to as "compound 6".

In another preferred embodiment, X is S; $R_1$ is H; $R_2$ and $R_3$ are ethyl; ring A is an unsaturated ring having two additional double bonds; and $Z_1$–$Z_8$ are H. The compound has the formula (C2H5)2N-[structure]-S-[structure]-NH (7)

and will hereinafter be referred to as "compound 7".

In another preferred embodiment, X is S; $R_1$ is H; $R_2$ and $R_3$ are ethyl; ring A is an unsaturated ring having two additional double bonds; $Z_1$ is I; and $Z_2$–$Z_8$ are H. The compound has the formula (C2H5)2N-[structure]-S-[structure I]-NH (8)

and will hereinafter be referred to as "compound 8".

In another preferred embodiment, X is S; $R_1$ is benzyl; $R_2$ and $R_3$ are ethyl; ring A is an unsaturated ring having two additional double bonds; and $Z_1$–$Z_8$ are H. The compound has the formula (C2H5)2N-[structure]-S-[structure]-N(CH2C6H5) (9)

and will hereinafter be referred to as "compound 9".

In another preferred embodiment, X is S; $R_1$ is H; $R_2$ and $R_3$ are ethyl; ring A is a saturated ring; and $Zb_1$–$Z_8$ are H. The compound has the formula (C2H5)2N-[structure]-S-[structure]-NH (10)

and will hereinafter be referred to as "compound 10".

In another preferred embodiment, X is S; $R_1$ is H; $R_2$ and $R_3$ are ethyl; $Z_1$ is I; ring A is saturated; and $Z_2$–$Z_8$ are H. The compound has the formula (C2H5)2N-[structure]-S-[structure I]-NH (11)

and will hereinafter be referred to as "compound 11".

In another preferred embodiment. X is O; $R_1$ is H; $R_2$ is H; $R_3$ is ethyl; $Z_1$ and $Z_2$ are Br; ring A is unsaturated; and $Z_3$–$Z_8$ are H. The compound has the formula H(C2H5)N-[structure Br]-O-[structure Br]-NH (12)

and will hereinafter be referred to as "compound 12".

In all of the compounds described above as preferred embodiments, the compound may exist in the neutral form as shown or as a pharmaceutically acceptable salt.

The compounds are used in a method for killing cancer cells that involves contacting the cells with the compound and then exposing the cells to light of a predetermined wavelength (preferably red light, i.e. light having a maximum wavelength of about 640 nm).

The invention provides compounds useful for photo-inactivation of cancer cells. The compounds are preferentially retained by cancer cells as compared to normal cells, thus minimizing damage to surrounding normal tissue. Furthermore, the compounds are relatively non-toxic. The compounds exhibit enhanced triplet yields, e.g., as compared to dyes such as Nile Blue A, when exposed to light, giving them potent anti-cancer activity without the need for high light intensities or long exposure times.

Other features and advantages of the invention will be apparent from the following description of the preferred embodiments thereof, and from the claims.

DESCRIPTION OF THE PREFERRED EMBODIMENTS

We first briefly describe the drawings.

STRUCTURE

The compounds of the invention are benzophenoxazine (X=O), benzophenothiazine (X=S), and benzophenoselenazine (X=Se) dyes having the formulae above. They can be provided in neutral form or as pharmaceutically acceptable salts, e.g., acetates or chlorides. When administered to a patient in a dosage of 15 mg/kg/day to 200 mg/kg/day, the compounds are taken up by both normal and cancer cells, but are selectively retained by the cancer cells. Exposure to light kills the cancer cells with minimal damage to surrounding normal tissue. The particular dosage for effective anti-cancer treatment will depend on the photoactivity of the particular compound. For example, compound 10, in which X is sulfur and ring A is saturated, is more active than compound 2, in which X is oxygen and ring A is unsaturated; thus, the former compound would require a lower dosage.

All of the compounds have a nitrogen atom ($N^2$) that is double-bonded to the ring at ring carbon 5. They undergo a protonation-deprotonation reaction at this nitrogen. A representative protonation-deprotonation reaction is shown below for compound (2). The protonated form is shown as a chloride salt. For simplicity, only one of the many mesomeric structures is presented. It is the protonated form which absorbs red light and is photoactive.

Thus, shorter exposure times and/or lower light intensities can be used.

The triplet quantum yield is measured indirectly by meauring the efficacy of the compounds for generating singlet oxygen ($^1O_2$), which is a product of energy transfer from the triplet state of the compound to The pka of $N^2$ is between 5 and 11. Thus, within the cellular environment, some of the molecules exist in protonated form, while others exist in neutral form.

While applicant does not wish to be bound by any particular theory, it is believed that the ability of the compounds to protonate and deprotonate readily is related to their ability to be taken up readily by cells and to be preferentially retained in cancer cells. It is thought that as the compound nears a cell (normal or cancerous), it loses a proton and reverts to neutral form. Because the neutral form passes more easily through the cell membrane than the charged form, the compound is now readily taken up by the cell. Once inside the cell, it is reprotonated so that it now exists in photoactive form. This protonated form is preferentially retained in the cancer cells, while in normal cells there is a greater tendency for the compound to lose the proton and pass back out through the cell membrane.

Another feature influencing the cellular uptake of the compounds is their lipophilicity, as measured by their octanol-water partition coefficient. The partition coefficient (PC) is calculated according to the following equation:

$$PC = ]OD_B/OD_A - 1]x \text{ volume } H_2O/\text{volume octanol}$$

where $OD_B$ and $OD_A$ are the optical densities measured before and after partition, respectively. The volume of water and volume of octanol used in measuring PC are equal to make their ratio equal to one. The lower the value of PC, the more lipophilic the material is. The PC values measured for compounds 2-12 ranged from 0 to 0.119. In contrast, azure A and methylene blue, which are considered hydrophilic dyes, have PC values of 2.085 and .3.129, respectively. In general, increasing lipophilicity increases cellular uptake. The presence of ring A is particularly useful for increasing lipophilicity.

Incorporating halogens (particularly iodine) in the ring structure or including sulfur or selenium for group X are modifications which enhance the triplet quantum yield of the compounds upon exposure to light. Triplet yields are also enhanced by requiring at least one of $R_2$ or $R_3$ to be H when $Z_2$ or $Z_3$ is a halogen, and requiring both $R_2$ and $R_3$ to be H when both $Z_2$ and $Z_3$ are halogens. This latter requirement enhances triplet yields because steric interference between the R and Z groups is minimized in this way. Increased triplet guantum yields are desirable because the excited triplet state is believed to mediate photo-inactivation of cells, as described in Foote (1968) Science 162: 963-70; Grossweiner (1969) Photochem. Photobiol. 10: 183-91; and Spikes et al. (1967) Ann. Rev. Phys. Chem. 18: 409-36.

ground state oxygen. The 1,3-diphenylisobenzofuran bleaching method described in Wilson (1966) J. Am. Chem. Soc. 88: 2989-2902 and Gandin et al., Photochem. Photobiol. 37: 271-78 was used to measure singlet oxygen generation. In this procedure, a solution of the compound and the furan $^1O_2$ acceptor was illuminated with a waveband of light centered at 630 nm which was absorbed only by the compound. The rate of which the furan was consumed was followed spectrophotometrically (Perkin-Elmer Lambda 5 UV/VIS) by observing the decrease of an absorption band at 410 nm as a function of irradiation time. Rose bengal (Aldrich) was used as the standard for the determination of absolute guantum yields ($^1O_2$-0.76 in methanol). Since this dye absorbs 630 nm light ineffeciently, it was evaluated using an illuminating wave band centered at 550 nm. the intensity of the tungsten source was adjusted to give the same number of photons per unit time for both the 630 and 550 nm wave bands as measured by an IL700A radiometer.

In order to improve the accuracy in comparing the $^1O_2$ guantum efficiencies of the compounds, each compound was evaluated under similar experimental conditions. To insure that an equal number of photons was absorbed per unit time in all experiments, the concentration of each compound was adjusted to give an optical density = 1.00 at 630 nm. It is noted that because the compounds do not have identical absorption bands or extinction coefficients, a different concentration of each was required to achieve the specified optical density.

Typically, to 2.5 ml of methanol (Baker 'Photrex') containing 1.0 μl of acetic acid was added enough compound to give an optical density of 1.02±0.01 at 630 nm. An absorption spectrum in the 400-700 nm region was obtained for each sample in order to show that >97% of the compound existed in its protonated form. With the sample in place, the spectrometer was computer controlled to set the absorbance to 0.00 at 410 nm. An aliguot of freshly prepared 1,3-diphenylisobenzofuran in acetonitrile (25 μl) was added to give an optical density = 1.0±0.02 at 410 nm. This solution was illuminated with a filtered (630 or 550 nm interference filter, 10 nm FWHM) beam from a 500 W tungsten source. The rate of furan photoxidation was followed spectrophotometrically for one half-life.

The singlet oxygen yields for various compounds are shown in Table 1.

TABLE 1

| Compound | $^1O_2$ Yield |
|---|---|
| 2 | 0.036 |
| 3 | 0.5 |

TABLE 1-continued

| Compound | $^1O_2$ Yield |
| --- | --- |
| 4 | 0.008 |
| 5 | 0.007 |
| 6 | 0.034 |
| 7 | 0.024 |
| 8 | 0.170 |
| 9 | 0.021 |
| 10 | 0.3 |
| 11 | 0.65 |
| 12 | 0.082 |

Synthesis

The compounds are synthesized using known synthetic methods for preparing benzophenoxazines, benzophenothiazines, and benzophenoselenazines. Specific compounds were prepared as follows.

EXAMPLE 1

Compound 2, in the form of an acetic acid salt, was prepared as follows.

Five grams of Nile Blue A was dissolved in 200 ml of hot trifluoroethanol. To this blue solution was added 1 ml of glacial acetic acid and after the addition of 3.1 g of N-iodosuccinimide the resulting solution was heated at 90° C. with stirring for one hour. An additional sample (3.0 g) of N-iodosuccinimide was added to the solution; heating and stirring were continued for 15 minutes. A final 3.0 g sample of N-iodosuccinimide was added to the dark blue solution and after heating for 5 minutes the solvent was removed under vacuum. The dark blue residue was purified by column chromatography using a solid phase of silica gel (32–63 mesh) and an eluting solvent of methanol/methylene chloride (gradient starts 1/100 volume/volume; ends 9/100 v/v). The blue fractions that were shown to have an absorption maximum of 642 nm in methanol and to be homogeneous by tlc analysis (silica gel-methanol/methylene chloride: 5/100 v/v) were combined and evaporated to give 1.6 g of compound 2. The structure of the novel iodinated dye was established using NMR spectroscopy and high resolution mass spectroscopy.

EXAMPLE 2

Compound 3, in the form of a hydrochloride salt, was prepared as follows.

Six grams of Nile Blue A was dissolved in a solvent consisting of 210 ml of trifluoroethanol, 80ml glacial acetic acid, and 3 ml water. The solution was heated to 70° C. with stirring. To this dark blue solution was added 25 g of N-iodosuccinimide over a 30 minute period (temperature rose to 85° C.). The solvent was removed under vacuum. The residue was treated with 500 ml of methylene chloride and 100 ml of aqueous potassium carbonate. The methylene chloride layer was separated and the solvent removed under vacuum to give 5 g of a dark solid. A 2.0 g portion of this material was separated using column chromatography (silica gel 32–63 mesh; solvent gradient-methanol/methylene chloride starting at 0.5/100 v/v and ending 3/100 v/v) to give 0.7g of the free base form of compound 3. This material was converted into protonated form by treating a methanolic solution of the free base with an equivalent of hydrochloric acid. The compound had a absorption maximum of 620nm in methanol; NMR and high resolution mass spectral data were used to confirm the assigned structure.

Compound 12 was prepared in analogous fashion.

EXAMPLE 3

Compound 4, in the form of a hydrochloride salt, was prepared as follows.

A 0.400g sample of 6-iodonaphthlyl-1-amine was dissolved in 16 ml of glacial acetic acid. To this solution was added 0.430g of 4-nitroso-3-hydroxy-N, N-diethylaniline and 0.5 ml of concentrated hydrochloric acid. The resulting solution was stirred and heated to 120° C. while slowly adding 1.5 ml of water. After 2.5 hour at this temperature the solvent was removed under vacuum. The residue was washed several times with ethyl ether, and then purified by column chromatography (silica gel 32–63 mesh; solvent gradient starts at methanol/methylene chloride 0/100 v/v; ends at 8/100 v/v). The blue fractions that were homogeneous by tlc analysis (silica gel; methanol/methylene chloride-5/100 v/v) were combined and evaporated to give 70.0mg of the compound 4 having an absorption maximum of 633nm in methanol. An NMR spectrum was consistent with the assigned structure.

EXAMPLE 4

Compound 6, in the form of a hydrochloride salt, was prepared as follows.

A 0.050 sample of 5-amino-2-iodo-9diethylaminobenzo[a] phenoxazinium chloride was dissolved in 7 ml of trifluoroethanol and 0.2 ml of glacial acetic acid. To this room temperature blue solution was added 0.075g of N-iodosuccinimide. After 30 minutes the solvent was removed under vacuum. The residue was purified by column chromatography using a solid phase of silica gel and a gradient eluting solvent of methanol/methylene chloride starting at 1/100 v/v and ending with 3/100 v/v. The compound thus obtained was homogeneous by t/c analysis (silica gel; methanol/methylene chloride 1/10). The yield was 0.024g; the dye had a maximum absorption at 650nm in methanol and an NMR spectrum consistent with the assigned structure.

EXAMPLE 5

Compound 5, in the form of a hydrochloride salt, was prepared as follows.

A 200 mg sample of Nile Blue A was dissolved in 15 ml of trifluoroethanol. To this solution was added 50 ml of glacial acetic acid. While stirring the resulting solution at room temperature, 0.030 ml of bromine was added. A solid immediately separated from solution. After an additional 15 minutes of stirring, the solid was isolated by filtration, washed with ether, and dried, giving 0.240g of crude product. The dye was purified by preparative column chromatography using silica gel as the solid phase and a gradient solvent elutant of methanol/methylene chloride starting at 1/100 v/v and ending at 7/100 vv. Compound 5 (0.120g) was isolated in its free base form; it was converted to the protonated form by treatment with hydrochloric acid in methanol. The salt form of the dye had an absorption maximum at 64lnm in methanol and an NMR spectrum consistent with the assigned structure.

EXAMPLE 6

Compound 7, in the form of a hydrochloride salt, was prepared as follows.

0.5g of 1-naphthylamine and 1.0g of 2-amino-5-diethyl-aminophenylthiosulfuric acid were added to 20 ml of dimethylsulfoxide at room temperature and dissolved with stirring. To this solution was added 1.03g of potassium dichromate and the solution turned purple brown. The solution was stirred for 20 min. and then 350 ml of methanol and 40 ml of 1N HCl were added. This solution was stirred for 40 min. during which time it turned a deep cyan color. The solution was placed on a rotary evaporator and the methanol removed under reduced pressure to leave the dye in dimethylsulfoxide. This solution was slowly poured into 450 ml of water saturated with NaCl and the blue precipitate was filtered off and air dried to yield 0.925g. The crude dye was purified by column chromatography using a solid phase of silica gel (32–63 mesh) and an eluting solvent of methanol/methylene chloride (gradient starts 1/100 volume/volume; ends 14/100 v/v). The blue fractions that were shown to have an absorption maximum of 645nm in methanol and to be homogeneous by tlc (silica gel-methanol/methylene chloride: 10/100 v/v) were combined and evaporated to give 0.550g of compound 7. The structure of the novel compound was established by using NMR spectroscopy.

EXAMPLE 7

Compound 8, in the form of a hydrochloride salt, was prepared as follows.

0.15g of the dye from example 6 was iodinated as in example 1 at 50° C. for 20 min. to yield, after purification by column chromatography on the solid phase of silica gel, 0.15g of compound 8. The dye, which had an absorption maximum at 660mm in methanol, was homogeneous by tlc analysis (silica gel-methanol/methylene chloride: 10/100 v/v). The structure was confirmed by NMR.

EXAMPLE 8

Compound 9, in the form of a hydrochloride salt, was prepared as follows.

0.233g of N-benzyl-1-aminonaphthylene and 0.276g of 2-amino-5-diethyl-aminophenylthiosulfuric acid were combined with 0.294 g of potassium dichromate in 10 ml of dimethylsulfoxide following the procedure of example 6 to yield 0.23 g of compound 9 after purification by column chromatography on the solid phase silica gel (32–63 mesh). The dye, which had an absorption maximum of 658 mm in methanol, was homogeneous by TLC analysis (silica gel- methanol/methylene chloride: 10/100 v/v). The structure was confirmed by NMR.

EXAMPLE 9

Compound 10, in the form of a hydrochloride salt was prepared following the procedure of Example 6.

0.147g of 5,6,7,8-tetrahydro-1-naphthylamine and 0.276g of 2-amino-5-diethyl-aminophenylthiosulfuric acid were combined with 0.294g of potassium dichromate in 10 ml of dimethylsulfoxide to yield 0.040 g of compound 10 after purification by column chromatography on the solid phase silica gel (32–63 mesh). The dye, which had an absorption maximum of 628 nm in methanol, was homogeneous by TLC analysis (silica gel- methanol/methylene chloride: 10/100 v/v and 2 drops of glacial acetic acid). The structure was confirmed by NMR.

Compound 11, in the form of an acetic acid salt, was prepared from compound 10 following the procedure of example 1.

In Vitro Studies

The compounds were evaluated for their in vitro photoactivity and selectivity towards various cells.

A. Killing of Hep2 Carcinoma Cells

The dye-induced toxicity of compounds 2, 6, 7, 8, and 9 towards Hep2 human larynx carcinoma cells was evaluated as follows.

An appropriate number of cells ($0.5-2.0 \times 10^4$) was seeded in a 24 well, flat-bottomed Limbro plate using supplemented minimum Eagle's medium (MEM). Forty eight hours later, the subconfluent monolayers were washed twice with Hanks balanced salt solution (HBSS) and incubated with $5 \times 10^{-7}$M of each dye in 5% aqueous glucose solution for 10 minutes at 37° C. The cells were immediately washed twice with HBSS and fresh growth medium was added. The cells were then cultured for an additional 6 hours; approximately half-way through this period, the growth medium was replaced with fresh medium. The cells were then irradiated in HBSS at 4° C. for 30 min. with an irradiance of 8mw/cm$^2$ (wavelength of irradiation =496–700 nm). Afterwards, th irradiated cells were replaced in complete medium and kept at 37° C.

Dye toxicity was evaluated 42 hours after the irradiation by measuring the cells' ability to carry out protein synthesis. Dye-free cells incubated in the dark were used as the control. The protein synthesis was assayed (Beckman LS8000 scintillation counter) according to the method of Varandani et al. (1982) Am. J. Physiol. 243: E132–138 by following tritiated leucine (5μCi 0.5 ml$^{-1}$ modified Waymouth's medium; final SA=130 mCimM$^{-1}$) incorporation into total cellular protein over a 3 hour period at 37° C.

Figure 1:
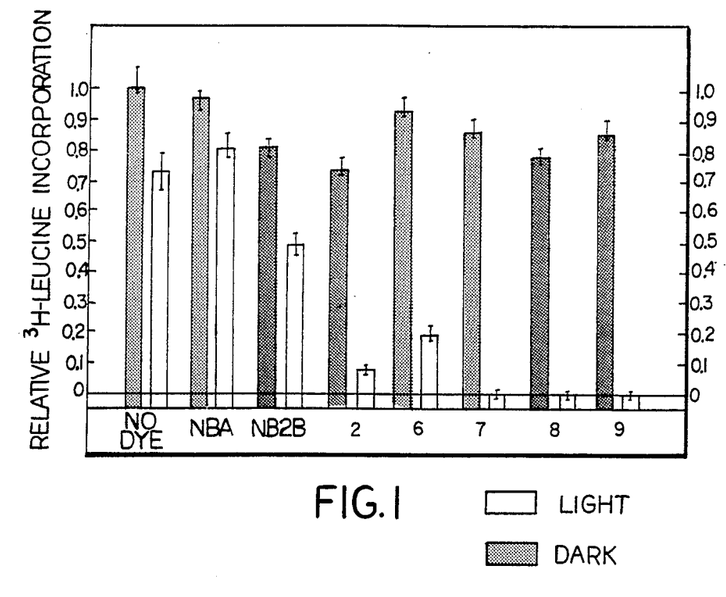
FIG. 1 is a bar graph showing the photo-induced killing of Hep2 human larynx carcinoma cells sensitized with various dyes.

The results of the evaluation are shown in FIG. 1. Nile Blue A (NBA) and Nile Blue 2B (NB2B), two well-known dyes that have been shown to localize in tumor cells, are included for the sake of comparison. As FIG. 1 demonstrates, the dyes of the invention had dark toxicities comparable to those of NBA and NB2B, but significantly higher light toxicities. Compounds 7, 8, and 9, in which X is sulfur, were particularly potent.

B. Killing of Various Carcinomata and Sarcoma Cells

Figure 2:
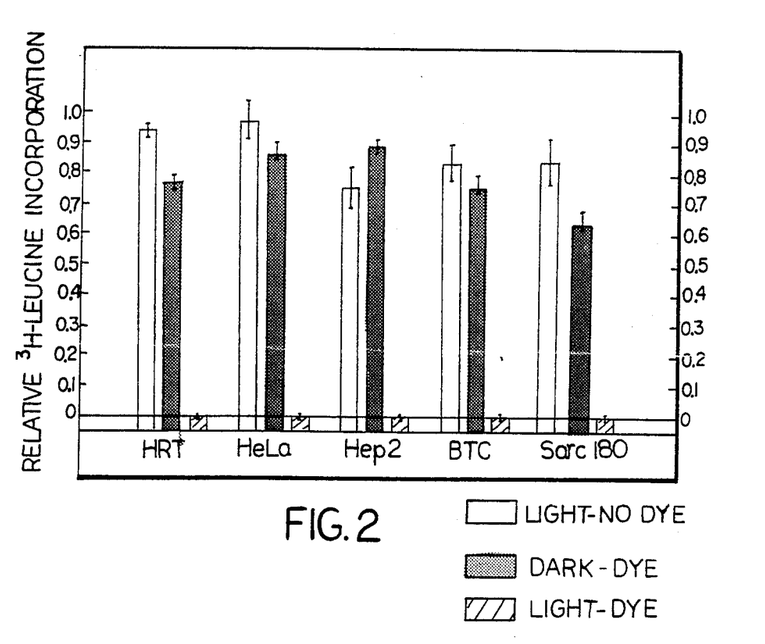
FIG. 2 is a bar graph showing the photo-induced killing of various dye-sensitized human carcinomata and murine sarcoma cells.

The susceptibility of three additional carcinomata cell lines (HRC human rectal carcinoma cells, HeLa human cervical carcinoma cells,and BTC human bladder carcinoma cells) and one sarcoma cell line (Sarc 180 murine sarcoma) to compound 2 was evaluated, as well as Hep2 cells. The procedure described above for Hep2 cells was followed using a dye concentration of $1.25 \times 10^{-6}$M in 5g aqueous glucose solution and exposure 3 hours later to an irradiance of 8mW/cm$^2$ (irradiance wavelength=495–700nm). The results were compared to those obtained from dye-free cells exposed to light and to dye-containing cells held in the dark. The results of this experiment, shown in FIG. 2, demonstrate that compound 2 was effective against a wide variety of cancer cells.

C. Differentiation Between Normal and Cancer Cells

Figure 3A:
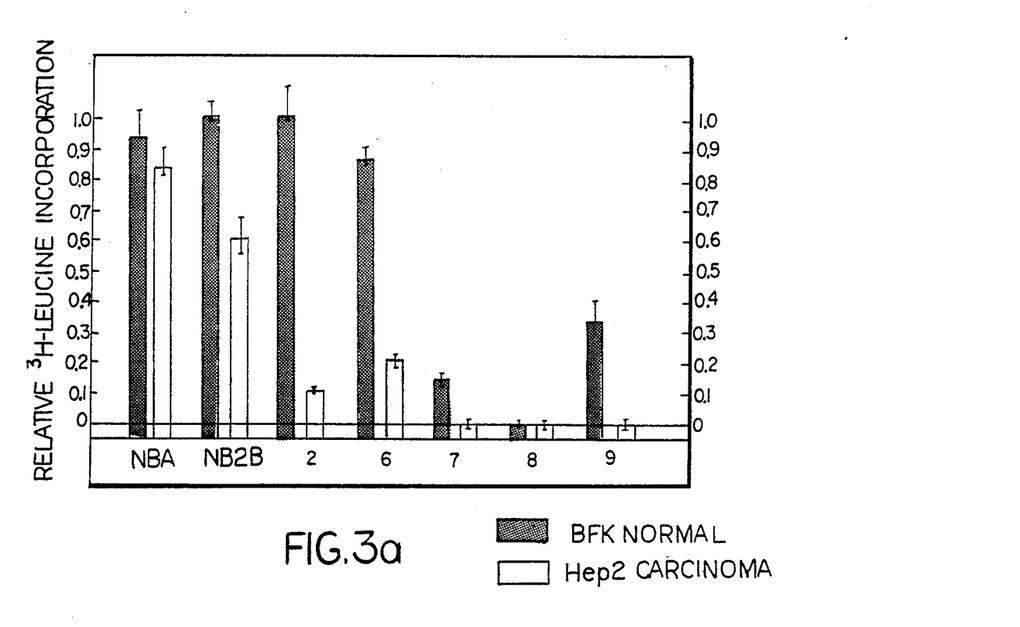
FIG. 3a is a bar graph showing the effect of various dyes on normal BFK cells and Hep2 carcinoma cells.

Two experiments were conducted to determine the effect of the dyes on normal versus cancer cells. In the first experiment, both Hep2 carcinoma cells and normal BFK bovine fetal kidney cells were treated with compounds 2, 6, 7, 8, and 9 following the procedure described above. Both types of cells were incubated for 10 minutes with $5\times10^{-7}$M dye in 5% aqueous glucose solution and irradiated 3 hours later for 30 minutes with an irradiance of 8mw/cm² (irradiation wavelength =495-700nm). NBA and NB2B dyes werg also used for comparative purposes. The results are shown in FIG. 3a. Compounds 2 and 6 showed excellent differentiation between normal and cancer cells. Although the selectivity of benzophenothiazine compounds 7, 8, and 9 was less pronounced, it may be that in light of the fact that the benzophenothiazines are generally more reactive than benzophenoxazines, the dosage used was simply too high.

Figure 3B:
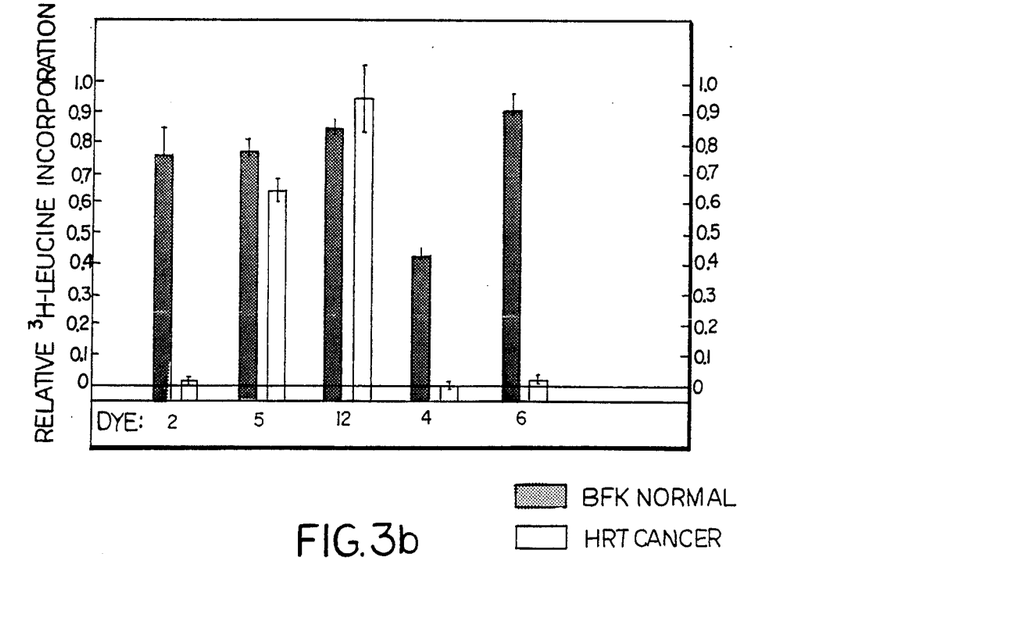
FIG. 3b is a bar graph showing the effect of various dyes on normal BFK cells and HRT carcinoma cells.

In the second experiment, both HRT carcinoma cells and BFK normal cells were treated with compounds 2, 4, 5, 6, and 12. The cells were incubated for 10 minutes with $5\times10^{-7}$M dye and irradiated 6 hours later for 30 minutes with an irradiance of 8mw/cm² (irradiance wavelength =495-700nm). The results are shown in FIG. 3b. Except for compound 12, all the dyes preferentially killed the carcinoma cells. However, the failure of compound 12 to exhibit a statistically significant preference for carcinoma cells is most likely attributable to the fact that at the pH of the cell growth medium (approximately 7.0) compound 12 exists predominantly in the neutral form (pkg of compound 12 is 5.7) which is not soluble in the growth medium. Lowering the pH of the growth medium to 6.0 increases the proportion of the protonated form which is more soluble in the growth medium. Thus, compound 12 (as well as compound 3, which has a similarly low pka value) would be expexted to show a preference for carcinoma cells in media having lower pH values.

In Vivo Studies

A mouse having a subcutaneous abdominal EMT-6 mammary tumor (which is not ordinarily photosensitive) 5mm in diameter was subcutaneously injected at the base of the neck with 2mg of compound 10 in 5% glucose solution. After four hours, the mouse was exposed to red light for 10 minutes (400 J/cm²). Subsequent examination 16 hours later of the exposed area revealed that the tumor was non-palpable and scabbed over, but surrounding tissue, which had also been exposed to red light, was unharmed. After several days, the scab fell off, leaving a scar. After 8 weeks, there was no regrowth of the tumor.

The tumors of control mice that were irradiated under the same conditions but which were not treated with dye continued to grow until the animals were destroyed.

Other embodiments are within the following claims.

We claim:

1. A compound having the formula wherein
X is O, S, or Se; each $R_1$, $R_2$, and $R_3$, independently, is H, lower alkyl, or aralkyl; ring A is a saturated or unsaturated ring; and each $Z_1$, $Z_2$, $Z_3$, $Z_4$, $Z_5$, $Z_6$, $Z_7$, and $Z_8$, independently, is H or a halogen, provided that when X is 0, at least one group Z is a halogen; when either $Z_2$ or $Z_3$ is a halogen, at least one of $R_2$ or $R_3$ is H; and when both $Z_2$ and $Z_3$ are halogens, both $R_2$ and $R_3$ are H;

or a pharmaceutically acceptable salt thereof.

2. The compound of claim 1 wherein the pka of said $N^2$ is between 5 and 11, inclusive, in aqueous solution.

3. The compound of claim 1 wherein X is O; $R_1$ is H; $R_2$ is H; $R_3$ is ethyl; $Z_1$ and $Z_2$ are Br; ring A is unsaturated; and $Z_3$-$Z_8$ are H, said compound having the formula or a pharmaceutically acceptable salt thereof.

4. The compound of claim 1 wherein X is O; $R_1$ is H; $R_2$ and $R_3$ are ethyl; A is an unsaturated ring; and $Z_2$-$Z_8$ are H, said compound having the formula or a pharmaceutically acceptable salt thereof.

5. The compound of claim 1 wherein X is O; $R_1$ is H; $R_2$ is H; $R_3$ is ethyl; $Z_1$ and $Z_2$ are I; ring A is an unsaturated ring: and $Z_{3-Z8}$ are H, said compound having the formula or a pharmaceutically acceptable salt thereof.

6. The compound of claim 1 wherein X is O; $R_1$ is H; $R_2$ and $R_3$ are ethyl; ring A is unsaturated; $Z_6$ is I; and $Z_1$-$Z_5$ and $Z_7$-$Z_8$ are H, said compound having the formula or a pharmaceutically acceptable salt thereof.

7. The compound of claim 1 wherein X is O; $R_1$ is H; $R_2$ and $R_3$ are ethyl; Z is Br; ring A is unsaturated; and $Z_2-Z_8$ are H, said compound having the formula or a pharmaceutically acceptable salt thereof.

8. The compound of claim 1 wherein X is O; $R_1$ is H; $R_2$ and $R_3$ are ethyl; $Z_1$ and $R_6$ are I; ring A is unsaturated; and $Z_2-Z_5$ an $Z_7-Z_8$ are H, said compound having the formula or a pharmaceutically acceptable salt thereof.

9. The compound of claim 1 wherein X is S; $R_1$ is H; $R_2$ and $R_3$ are ethyl; ring A is unsaturated; and $Z_1-Z_8$ are H. said compound having the formula or a pharmaceutically acceptable salt thereof.

10. The compound of claim 1 wherein X is S; $R_1$ is H; $R_2$ and $R_3$ are ethyl; ring A is unsaturated; $Z_1$ is I; and $Z_2-Z_8$ are H, said compound having the formula or a pharmaceutically acceptable salt thereof.

11. The compound of claim 1 wherein X is S; $R_1$ is benzyl; $R_2$ and $R_3$ are ethyl; ring A is unsaturated; and $Z_1-Z_8$ are H, said compound having the formula or a pharmaceutically acceptable salt thereof.

12. The compound of claim 1 wherein X is S; $R_1$ is H; $R_2$ and $R_3$ are ethyl; ring A is saturated; and $Z_1-Z_8$ are H, said compound having the formula or a pharmaceutically acceptable salt thereof.

13. The compound of claim 1 wherein X is S; $R_1$ is H; $R_2$ and $R_3$ are ethyl; $Z_1$ is I; ring A is saturated; and $Z_2-Z_8$ are H, said compound having the formula or a pharmaceutically acceptable salt thereof.

* * * * *

UNITED STATES PATENT AND TRADEMARK OFFICE
CERTIFICATE OF CORRECTION

PATENT NO. : 4,962,197

DATED : October 9, 1990

INVENTOR(S) : James W. Foley et al

It is certified that error appears in the above-identified patent and that said Letters Patent is hereby corrected as shown below:

Col. 12, claim 4, line 26, before "A", insert --$Z_1$ is I; ring--;

Col. 12, claim 4, in the formula, make the correction as shown below:

Col. 12, claim 5, in the formula, make the correction as shown below:

UNITED STATES PATENT AND TRADEMARK OFFICE
CERTIFICATE OF CORRECTION

PATENT NO. : 4,962,197

DATED : October 9, 1990

INVENTOR(S) : James W. Foley et al

It is certified that error appears in the above-identified patent and that said Letters Patent is hereby corrected as shown below:

Col. 13, claim 7, line 2, change "Z" to --$Z_1$--;

Col. 13, claim 8, line 18, change "$R_6$" to --$Z_6$--;

Col. 13, claim 8, lines 20-30, correct the formula as shown below:

UNITED STATES PATENT AND TRADEMARK OFFICE
CERTIFICATE OF CORRECTION

PATENT NO. : 4,962,197

DATED : October 9, 1990

INVENTOR(S) : James W. Foley et al

It is certified that error appears in the above-identified patent and that said Letters Patent is hereby corrected as shown below:

Col. 14, claim 10, correct the formula as shown below:

Signed and Sealed this

Ninth Day of June, 1992

Attest:

DOUGLAS B. COMER

Attesting Officer

Acting Commissioner of Patents and Trademarks